United States Patent
Katsman et al.

(10) Patent No.: US 7,457,672 B2
(45) Date of Patent: Nov. 25, 2008

(54) METHOD AND APPARATUS FOR EXPORTING ULTRASOUND DATA

(75) Inventors: Igor Katsman, Haifa (IL); Paul Joseph O'Dea, Muskego, WI (US); Hemen Oza, Waukesha, WI (US); Gregory Rachvalsky, Haifa (IL); Alexander Sokulin, Tivon (IL); Arcady Kempinski, Haifa (IL)

(73) Assignee: General Electric Company, Schenectady, NY (US)

( * ) Notice: Subject to any disclaimer, the term of this patent is extended or adjusted under 35 U.S.C. 154(b) by 568 days.

(21) Appl. No.: 10/659,144

(22) Filed: Sep. 10, 2003

(65) Prior Publication Data

US 2005/0054921 A1 Mar. 10, 2005

(51) Int. Cl.
*G05B 11/01* (2006.01)

(52) U.S. Cl. ................ 700/17; 600/443; 600/437; 382/128; 700/83; 705/2; 710/65

(58) Field of Classification Search ............ 600/437, 600/443; 382/128; 700/17, 83; 710/65; 707/10; 715/751; 705/2

See application file for complete search history.

(56) References Cited

U.S. PATENT DOCUMENTS

| | | | | |
|---|---|---|---|---|
| 5,715,823 A * | 2/1998 | Wood et al. | | 600/437 |
| 5,724,101 A * | 3/1998 | Haskin | | 348/441 |
| 5,920,317 A | 7/1999 | McDonald | | |
| 5,986,662 A * | 11/1999 | Argiro et al. | | 345/424 |
| 6,032,120 A | 2/2000 | Rock et al. | | |
| 6,042,545 A | 3/2000 | Hossack et al. | | |
| 6,213,944 B1 * | 4/2001 | Miller et al. | | 600/437 |
| 6,224,551 B1 | 5/2001 | Mullen | | |
| 6,351,547 B1 * | 2/2002 | Johnson et al. | | 382/128 |
| 6,370,413 B1 | 4/2002 | Alvarez et al. | | |
| 6,381,029 B1 * | 4/2002 | Tipirneni | | 358/1.14 |
| 6,424,996 B1 * | 7/2002 | Killcommons et al. | | 709/206 |
| 6,471,649 B1 * | 10/2002 | Saccardo et al. | | 600/437 |
| 6,501,818 B1 * | 12/2002 | Ali et al. | | 378/4 |
| 6,558,329 B1 | 5/2003 | Gatzke | | |
| 6,572,548 B2 | 6/2003 | Cerofolini | | |
| 6,659,953 B1 * | 12/2003 | Sumanaweera et al. | | 600/443 |
| 6,678,764 B2 * | 1/2004 | Parvulescu et al. | | 710/65 |
| 6,716,172 B1 * | 4/2004 | Kerby et al. | | 600/443 |
| 2003/0069503 A1 | 4/2003 | Susumu | | |
| 2004/0061889 A1 * | 4/2004 | Wood et al. | | 358/1.15 |

FOREIGN PATENT DOCUMENTS

| | | |
|---|---|---|
| JP | 2000 194836 A | 7/2000 |
| JP | 2000 259747 A | 9/2000 |

OTHER PUBLICATIONS

French Search Report; French Pat App No. 0409405, filed Sep. 6, 2004, Applicant-GE Med Systems Global Tech Co, LLC, GE Dkt No. 15UL137992, Date: Sep. 15, 2005, 1 pg.

* cited by examiner

*Primary Examiner*—Brian L. Casler
*Assistant Examiner*—John F Ramirez
(74) *Attorney, Agent, or Firm*—The Small Patent Law Group; Dean D. Small (57) ABSTRACT

A method and system for exporting ultrasound data is provided. The method includes accessing ultrasound data stored within an ultrasound system. The ultrasound data is stored in an ultrasound system readable format. The method further includes converting the ultrasound system readable format data to a user device readable format data for export from the ultrasound system and access via a user device.

24 Claims, 9 Drawing Sheets

METHOD AND APPARATUS FOR EXPORTING ULTRASOUND DATA

BACKGROUND OF THE INVENTION

This invention relates generally to ultrasound systems and, more particularly, to methods and devices for exporting ultrasound data from ultrasound systems.

Ultrasound systems provide high quality images, Doppler sound, textual information and other types of data. However, and particularly with respect to the high quality images, these images are formatted such that access to view the images is limited to devices having a specific viewer for the ultrasound image format (e.g., DICOM workstation). Thus, individuals (e.g., doctors and patients) that desire or need to review the images, may not be easily able to view the images or other types of data. For example, the individual may not have direct access to an ultrasound system or DICOM viewer needed to view the images due to time or location constraints. The individual must then locate a system to view the images (e.g., a system able to access the archived data in DICOM or other proprietary format), such as an available ultrasound machine or a special dedicated workstation (e.g., DICOM workstation or PAC machine). Thus, the review process is often inconvenient due to timing limitations, constraints on usage of dedicated hardware/software, and limitations of functionality of the dedicated software and dedicated data format (e.g., size of archived data).

Additionally, ultrasound images may be given to patients after scanning. For example, a hospital, as a complimentary service, may provide to patients, still pictures or image loops of a baby of a pregnant patient. These images are typically provided on a paper printout or printed and scanned to be provided on a VHS tape. Thus, the patient is provided with images on limited formats having limited viewing options and limited opportunity to share the images with others.

BRIEF DESCRIPTION OF THE INVENTION

In one exemplary embodiment, a method for providing ultrasound data for access with a user device is provided. The method includes accessing ultrasound data stored within an ultrasound system. The ultrasound data is stored in an ultrasound system readable format. The method further includes converting the ultrasound system readable format data to a user device readable format data for export from the ultrasound system and access via a user device.

In another exemplary embodiment, a user interface for an ultrasound system is provided. The user interface includes a scanner view control portion for selecting ultrasound data for converting and transferring to an external medium and a media view control portion for viewing ultrasound data converted and transferred to an external medium, The user interface also includes a scanner image control portion for controlling the conversion and transfer of the ultrasound data.

DETAILED DESCRIPTION OF THE INVENTION

Exemplary embodiments of ultrasound systems and methods for exporting ultrasound images are described in detail below. A detailed description of exemplary ultrasound systems will first be provided followed by a detailed description of various embodiments of methods and systems for exporting ultrasound images.

Figure 1:
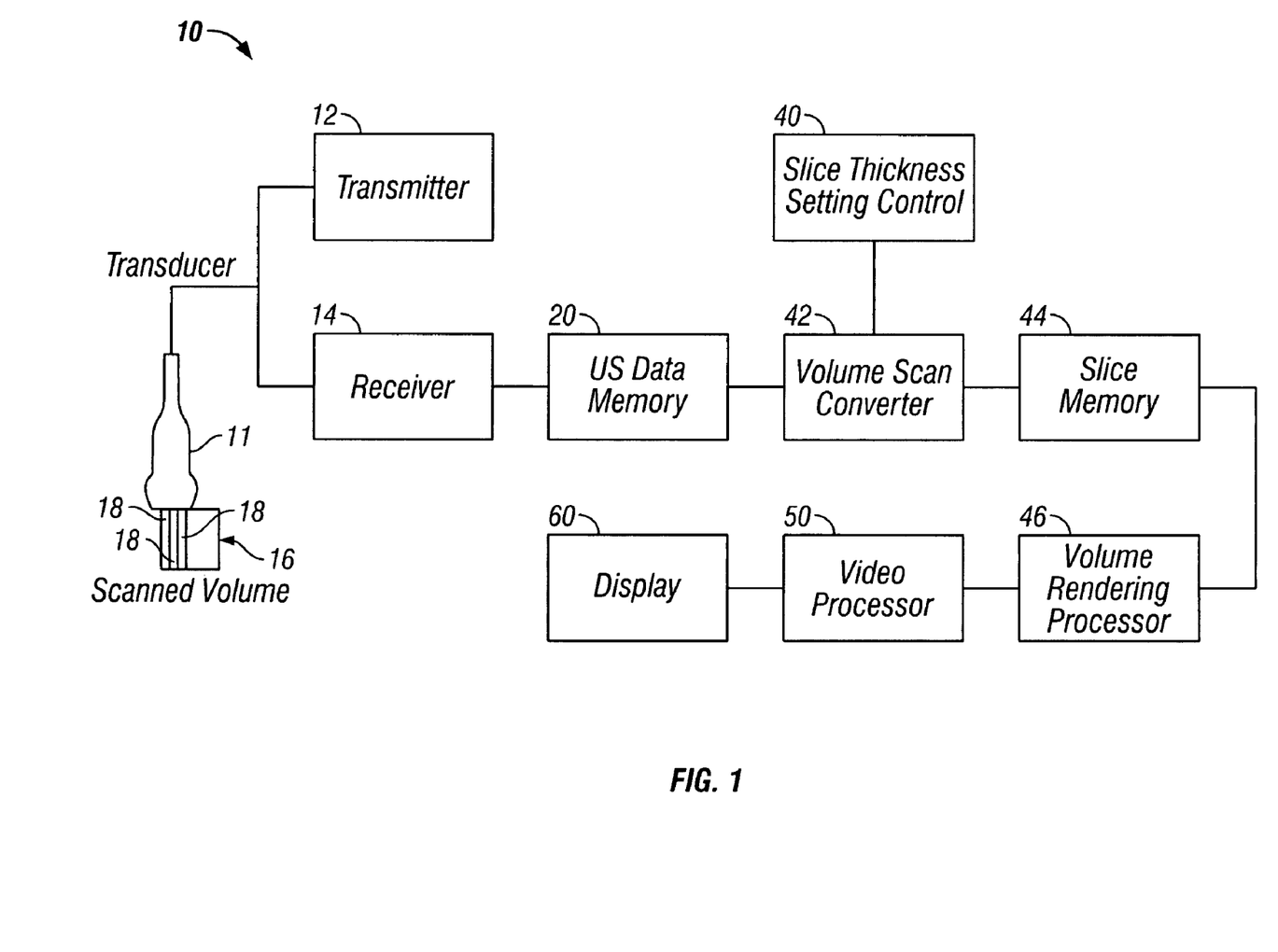
FIG. 1 is a block diagram of an ultrasound system in accordance with one exemplary embodiment of the present invention.

FIG. 1 illustrates a block diagram of an exemplary embodiment of an ultrasound system 10. The ultrasound system 10 includes a probe 11, such as, for example, a transducer, connected to a transmitter 12 and a receiver 14. The probe 11 transmits ultrasonic pulses and receives echoes from structures inside a scanned ultrasound volume 16. A memory 20 stores ultrasound data from the receiver 14 derived from the scanned ultrasound volume 16. The volume 16 may be obtained by various techniques, including, for example, 3D scanning, real-time 3D imaging, volume scanning, 2D scanning with transducers having positioning sensors, freehand scanning using a Voxel correlation technique, 2D or matrix array transducers and the like.

The probe 11 is moved, such as along a linear or arcuate path, while scanning a region of interest (ROI). At each linear or arcuate position, the probe 11 obtains scan planes 18. The scan planes 18 are collected for a thickness, such as from a group or set of adjacent scan planes 18. The scan planes 18 are stored in the memory 20, and then passed to a volume scan converter 42. In some embodiments, the probe 11 may obtain lines instead of the scan planes 18, and the memory 20 may store lines obtained by the probe 11 rather than the scan planes 18. The volume scan converter 42 may store lines obtained by the probe 11 rather than the scan planes 18. The volume scan converter 42 receives a slice thickness setting from a slice thickness setting control 40, which identifies the thickness of a slice to be created from the scan planes 18. The volume scan converter 42 creates a data slice from multiple adjacent scan planes 18. The number of adjacent scan planes 18 that are obtained to form each data slice is dependent upon the thickness selected by the slice thickness setting control 40. The data slice is stored in slice memory 44 and is accessed by a volume rendering processor 46. The volume rendering processor 46 performs volume rendering upon the data slice. The output of the volume rendering processor 46 is passed to a video processor 50 and a display 60 for viewing.

The position of each echo signal sample (Voxel) is defined in terms of geometrical accuracy (i.e., the distance from one Voxel to the next) and ultrasonic response (and derived values from the ultrasonic response). Suitable ultrasonic responses include gray scale values, color flow values, and angio or power Doppler information.

Figure 2:
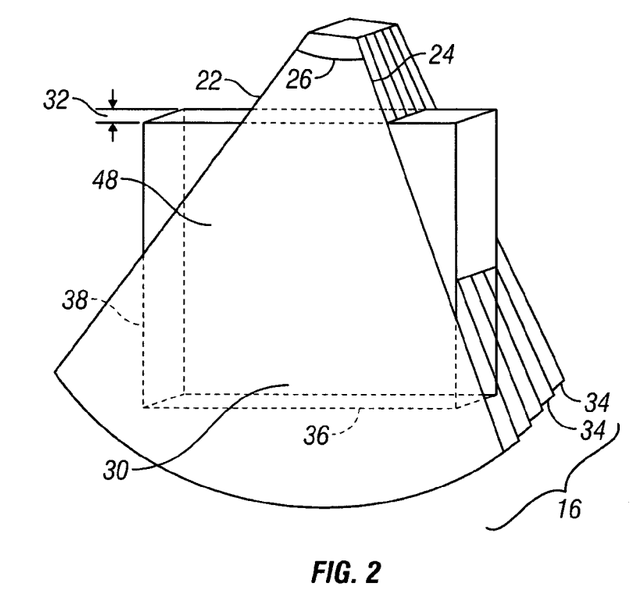
FIG. 2 is a perspective view of a real-time 4D volume acquired by the system of FIG. 1 in accordance with an exemplary embodiment of the present invention.

FIG. 2 illustrates a real-time 4D volume 16 acquired by the ultrasound system 10 of FIG. 1. It should be noted that the ultrasound system 100 of FIG. 3 as described below may also be used to acquire the real-time 4D volume 16. The volume 16 includes a sector shaped cross-section with radial borders 22 and 24 diverging from one another at an angle 26. The probe 11 (shown in FIG. 1) electronically focuses and directs ultrasound firings longitudinally to scan along adjacent scan lines in each scan plane 18 and electronically or mechanically focuses and directs ultrasound firings laterally to scan adjacent scan planes 18. Scan planes 18 obtained by the probe 11, and as illustrated in FIG. 1, are stored in the memory 20 and are scan converted from spherical to Cartesian coordinates by the volume scan converter 42. A volume comprising multiple scan planes is output from the volume scan converter 42 and stored in the slice memory 44 as a rendering box 30. The rendering box 30 in the slice memory 44 is formed from multiple adjacent image planes 34.

The rendering box 30 may be defined in size by an operator to have a slice thickness 32, width 36 and height 38. The volume scan converter 42 may be controlled by the slice thickness setting control 40 to adjust the thickness parameter of the slice to form a rendering box 30 of the desired thickness. The rendering box 30 designates the portion of the scanned volume 16 that is volume rendered. The volume rendering processor 46 accesses the slice memory 44 and renders along the slice thickness 32 of the rendering box 30.

Referring now to FIGS. 1 and 2, during operation, a 3D slice having a pre-defined, substantially constant thickness (also referred to as the rendering box 30) is acquired by the slice thickness setting control 40 and is processed in the volume scan converter 42. The echo data representing the rendering box 30 may be stored in the slice memory 44. Predefined thicknesses between about 2 mm and about 20 mm are typical, however, thicknesses less than about 2 mm or greater than about 20 mm may also be suitable depending on the application and the size of the area to be scanned. The slice thickness setting control 40 may include a rotatable knob with discrete or continuous thickness settings.

The volume rendering processor 46 projects the rendering box 30 onto an image portion 48 of an image plane 34. Following processing in the volume rendering processor 46, the pixel data in the image portion 48 may pass through a video processor 50 and then to a display 60. The rendering box 30 may be located at any position and oriented at any direction within the scanned volume 16. In some situations, depending on the size of the region being scanned, it may be advantageous for the rendering box 30 to be only a small portion of the scanned volume 16.

Figure 3:
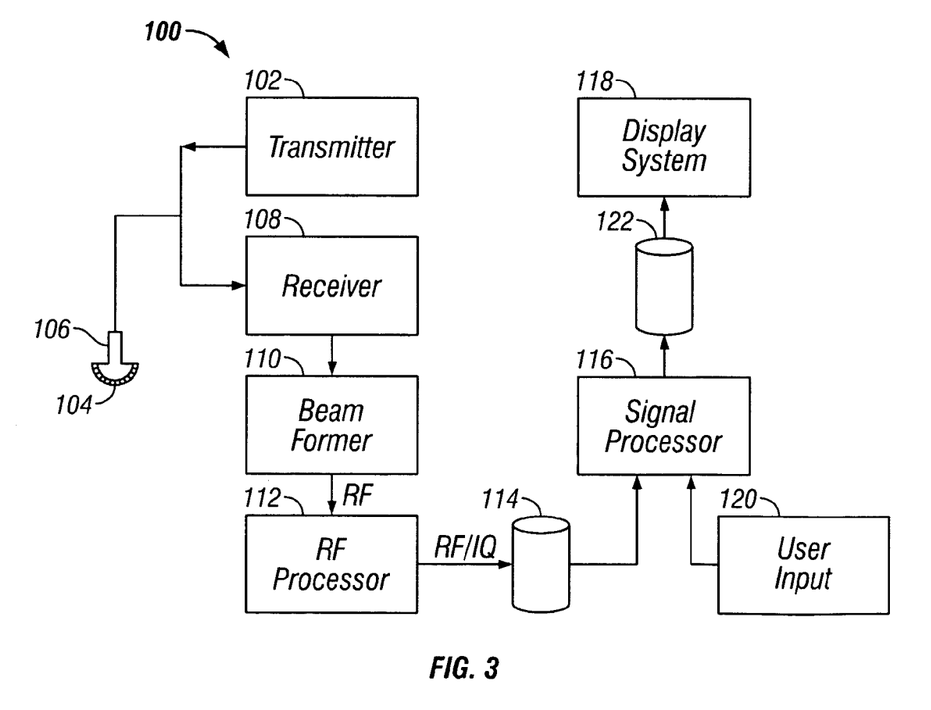
FIG. 3 is an ultrasound system in accordance with another exemplary embodiment of the present invention.

FIG. 3 illustrates a block diagram of another exemplary embodiment of an ultrasound system 100. The ultrasound system 100 includes a transmitter 102 that drives transducers 104 within a probe 106 to emit pulsed ultrasonic signals into a body. A variety of geometries may be used. The ultrasonic signals are back-scattered from structures in the body, like blood cells or muscular tissue, to produce echoes that return to the transducers 104. The echoes are received by a receiver 108. The received echoes are passed through a beamformer 110, which performs beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to an RF/IQ buffer 114 for temporary storage. A user input device may be used to control operation of the ultrasound system 100, including, to control the input of patient data, scan parameters, a change of scan mode, and the like.

The ultrasound system 100 also includes a signal processor 116 to process the acquired ultrasound data (i.e., RF signal data or IQ data pairs) and prepare frames of ultrasound data for display on display system 118. The signal processor 116 is adapted to perform one or more processing operations according to a plurality of selectable ultrasound modalities on the acquired ultrasound data. Acquired ultrasound data may be processed in real-time during a scanning session as the echo signals are received. Additionally or alternatively, the ultrasound data may be stored temporarily in the RF/IQ buffer 114 during a scanning session and processed in less than real-time in a live or off-line operation.

The ultrasound system 100 may continuously acquire ultrasound data at a frame rate that exceeds fifty frames per second, which is the approximate perception rate of the human eye. The acquired ultrasound data is displayed on the display system 118 at a slower frame-rate. An image buffer 122 is included for storing processed frames of acquired ultrasound data that are not scheduled to be displayed immediately. In an exemplary embodiment, the image buffer 122 is of sufficient capacity to store at least several seconds worth of frames of ultrasound data. The frames of ultrasound data are stored in a manner to facilitate retrieval thereof according to its order or time of acquisition. The image buffer 122 may comprise any known data storage medium.

The frames of ultrasound data, such as, for example, scanned images, viewed on the display 60 (shown in FIG. 1) or display system 118 (shown in FIG. 2) may be exported and viewed on a user device (e.g., computer) with the of various embodiments of methods and systems for exporting ultrasound images. In general, various embodiments of the present invention convert the ultrasound system readable format data (e.g., DICOM or other proprietary ultrasound format) to a user device readable format data (e.g., Photographic Experts Group (JPEG) format, Moving Pictures Experts Group (MPEG) format, Hypertext Markup Language (HTML) format, Portable Document Format (PDF), a word processor or spreadsheet format, etc.) for export to a medium (e.g., compact disc read-only-memory (CD ROM), magneto optical disc (MOD), digital versatile disc (DVD), Universal Serial Bus (USB) device, removable memory device, etc.) that is accessible by a user device. It should be noted that the ultrasound data may be exported to the medium via a hardwired communication link (e.g., CD ROM writer connected to the ultrasound system 10 or 100) or via a wireless communication link (e.g., a wireless handheld device communicating with the ultrasound system 10 or 100 via a wireless protocol). Further, the medium may be a local device (e.g., removable physical device or component) or may be a remote device (e.g., a mapped drive on a network).

Figure 4:
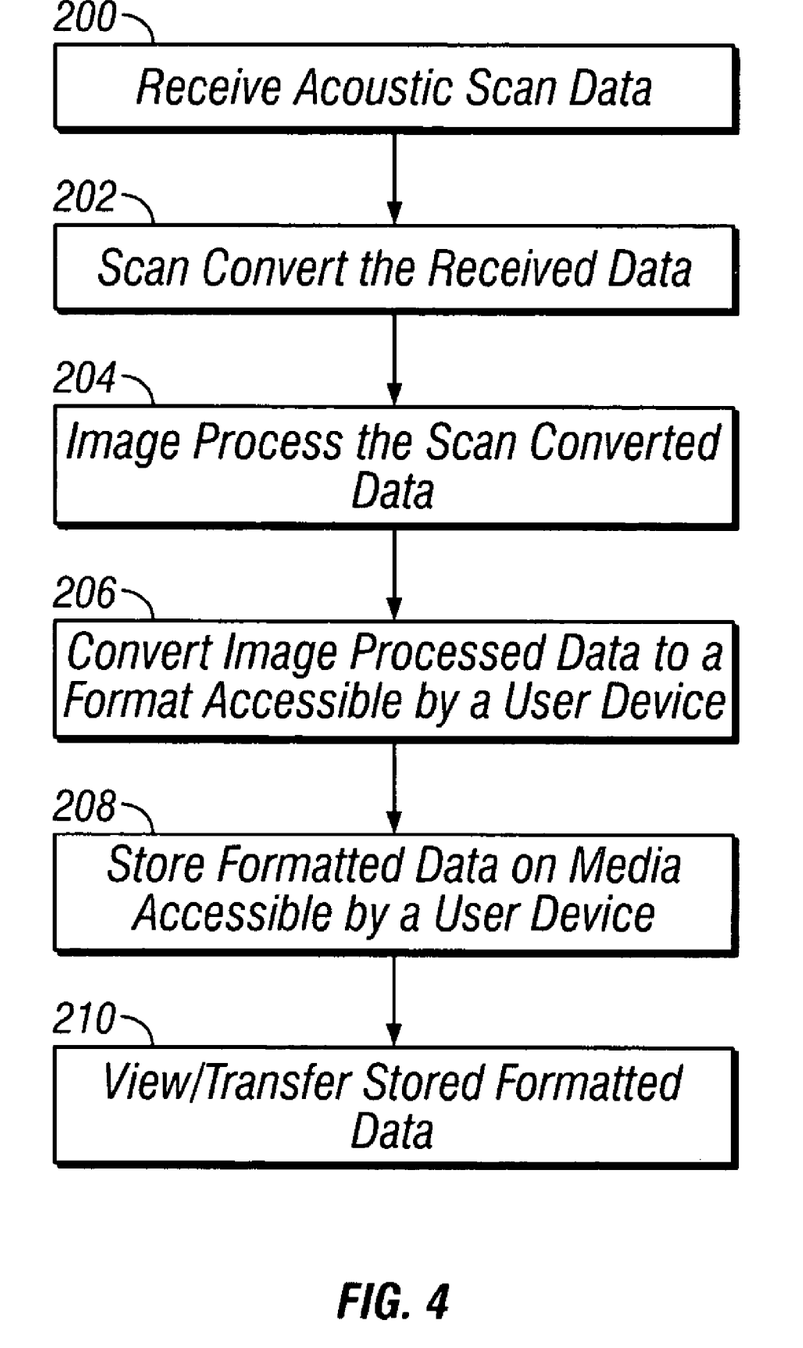
FIG. 4 is a flowchart illustrating an ultrasound image export process in accordance with an exemplary embodiment of the present invention.

An exemplary embodiment of an ultrasound image export process is shown in FIG. 4. Specifically, at step 200, acoustic scan data (e.g., ultrasound information) is received by the ultrasound systems 10 and 100 as described above. The received data is then scan converted at step 202, for example, using scan conversion techniques or processes provided as part of ultrasound systems (e.g., a scan conversion module). One example of a scan conversion process that may be used is described in U.S. Pat. No. 6,325,759 entitled "Ultrasound Imaging System." However, any suitable scan conversion process, for example, based upon system or scanner requirements or needs may be used. The scan conversion includes converting the beams and/or vectors of the acoustic scan data to pixels (e.g., ultrasound system readable format). For example, the acoustic scan data provided in a R-Theta polar space or format is converted to pixels provided in an X-Y Cartesian space or format.

The scan converted data (e.g., pixel data) is then image processed, for example, using noise reduction techniques (e.g., median filtering), resolution improvement techniques (e.g., digital adjustment of gray-scale imaging parameters), etc. at step 204. This image processing may include processing the scan converted data to produce, for example, improved images (e.g., images with reduced distortions or reduced noise interference effects) representing the acoustic scan data, and which may be displayed, for example, on the display 60 (shown in FIG. 1) or the display system 118 (shown in FIG. 3).

The image processed data (e.g., improved image quality pixel data) is then converted at step 206 to a format accessible by a user device (e.g., user device readable format). For example, the pixel data may be converted to JPEG, MPEG, HTML or PDF images for viewing on a computer. The formatted images are then stored on a medium/media accessible by the user device at step 208 (e.g., CD ROM, MOD, DVD, etc.). In an exemplary embodiment, the ultrasound system 10 or 100 includes a recording device, for example, a CD, DVD or MOD writer, for storing the formatted image directly to a CD, DVD or MOD, respectively. In such a case, the CD, DVD or MOD includes an embedded viewer for viewing the images that auto executes upon insertion of the media into a user device (e.g., inserting CD into computer CD drive). The viewer may be configured based upon the requirements of the user device. It should be noted that the images stored on the media may be still images (e.g., JPEGs converted from a single scan image) or cine loops of a series of images (e.g., MPEGs converted from a series of scan images). The formatted images stored on the medium/media may then, for example, be viewed (e.g., on a computer screen using the embedded viewer) or transferred (e.g., emailed to a doctor) for viewing on another user device (e.g., remote computer) at step 210.

Figure 5:
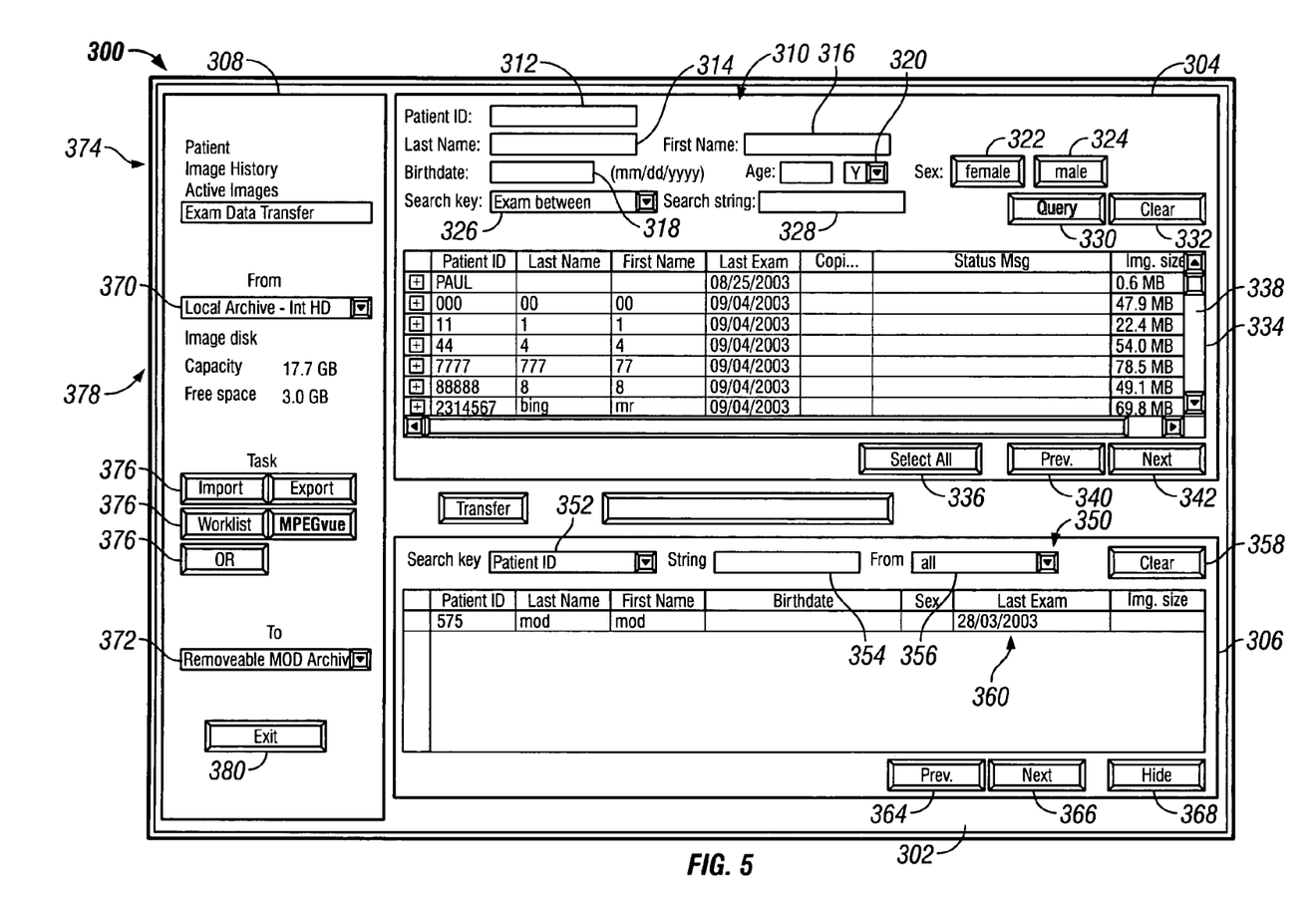
FIG. 5 is an exemplary embodiment of a user interface of an ultrasound system displaying an export image screen.

An exemplary embodiment of a user interface 300 for controlling the export of the ultrasound images is shown in FIG. 5. The user interface 300, may be provided, for example, as part of the user input 120 (shown in FIG. 3). Specifically, FIG. 5 is an exemplary embodiment of the user interface 300 displaying an export image screen/page 302 that may be displayed on the display 60 (shown in FIG. 1) or display system 118 (shown in FIG. 3). The export image screen/page 302 allows a user to determine specific ultrasound data (e.g., ultrasound images) to be converted and exported. The export image screen/page 302 includes a scanner view control portion 304, a media view control portion 306 and a scanner image control portion 308. The scanner view control portion 304 allows a user to search for and view the available images stored on the ultrasound system 10 or 100 for export and select specific ultrasound images for export. The media view control portion 306 allows a user to search for and determine ultrasound images or files stored on external media (e.g., CD ROM). The scanner image control portion 308 allows a user to select different modes of operation for the user interface 300.

In particular, the scanner view control portion 304 includes a search portion 310 that allows a user to search the available images on the ultrasound system 10 or 100. For example, the search portion 310 may include a Patient ID field 312, allowing for searching based upon an identification number (e.g., hospital ID number) for example, for a patient, a Last Name field 314 and a First Name field 316 allowing for searching based upon a name (e.g., patient's name), and Birthdate field 318 and an Age field 320 allowing for searching based upon a birth date and age. Further, Sex selection members 322 and 324 (e.g., selectable buttons) allow for searching based upon sex (e.g., patient's sex). A user may also search the available ultrasound images based on a Search key field 326, which as shown, is configured as a pull-down list with predetermined search criteria. A search also may be defined using a Search field 328, wherein a user may enter search terms. Upon entering one or more desired search terms, a user selects a Query selection member 330, which initiates a search of the available ultrasound data (e.g., ultrasound images stored on the ultrasound machine). A user may also clear the search criteria using a Clear selection member 332 (e.g., when a user desires to enter a new search). Although buttons and pull-down menus/lists are shown in the exemplary embodiments, and other selection means also may be used, such as, for example, check boxes.

After selecting the Query selection member 330, thereby initiating a search, the results are displayed in a results portion 334 (e.g., results list). The results portion 334 lists the ultrasound images (e.g., ultrasound files) satisfying the search criteria. The information listed may include for each ultrasound file, the following: patient identification (e.g., internal hospital identification number), patient first and last name, last exam date, the number of copies of the file, the status of the file and the size of the file or image. A user may then select some or all of the images or image files for transfer to external media. For example, a user may separately select each image or file (e.g., by highlighting the specific files) or select a Select All selection member 336 to select all images or files. It should be noted that a user may scroll through the search results using a scroll bar 338, a Prev. selection member 340 and Next selection member 342, or other suitable means (e.g., using external scroll control on ultrasound machine).

Once a user has selected the desired or required files to be transferred (i.e., exported) to the external medium/media, a user selects the Transfer selection member 344, which then converts and transfers the selected ultrasound images or files to the external media using, for example, the ultrasound image export process shown in FIG. 4 and described herein.

The media view control portion 306 includes a search portion 350 allowing a user to select the medium/media to determine the specific ultrasound images or files stored therein, and to view the ultrasound image files stored therein. For example, a Search key field 352, which as shown, is configured as a pull-down list with predetermined search criteria may be used to search the external medium/media, and may include the same, similar or different search criteria as the Search key field 326. A user may also enter a search using a String field 354, allowing a user to enter search terms on which to search. A From field 356 also allows a user to define the search field (e.g., search all ultrasound image files on the external medium). A user may also clear the search criteria using a Clear selection member 358 (e.g., when a user desires to enter a new search).

The media view control portion 306 also includes an ultrasound image/file list 360 displaying the ultrasound images and files on the external medium/media (e.g., files transferred after a user selects the Transfer selection member 344). Information may be provided regarding each ultrasound image or file, including, for example, patient identification, patient's first and last name, patient's birthdate and sex, date of last exam for the patient and image or file size. A user may scroll through the list, for example, using a Prev. selection member 364 and a Next selection member 366. It should be noted that the media view control portion 306 may be hidden (i.e., not displayed) by selecting a Hide selection member 368.

The scanner image control portion 308 allows a user to select the source and destination for the transfer of ultrasound images or files. Specifically, a From field 370 allows a user to select (e.g., from a drop down predetermined list) the source of the ultrasound images or files. This selection also defines the source (e.g., ultrasound image database) from which a user can search, for example, for particular images. A To field 372 allows a user to select (e.g., from a drop down predetermined list) the destination medium/media for the ultrasound images or files. Based upon the selection of the destination medium/media, the various embodiments will configure the ultrasound images or files for that media/medium (e.g., convert to a format for that medium/media). Alternatively, or in addition to, the ultrasound images or files may be converted to a predetermined format (e.g., JPEG) or a format selection field (not shown) may be provided to allow a user to select the particular format to which the ultrasound images or files are to be converted.

The scanner image control portion 308 also includes general control options, for example, a patient image selection portion 374, allowing a user to select specific images (e.g., active or archived) for display for a particular patient. Other control selection members 376 also may be provided to allow for importing and exporting images within the ultrasound system 10 or 100 or generating worklists for use during scanning operations. General information regarding the medium/media to which the ultrasound images or files may be transferred may be displayed on a media disk information portion 378 (e.g., capacity and free space on a particular MOD). An Exit selection member 380 is also provided to allow a user to exit the export image screen/page 302 and select, for example, another control screen, such as to control a particular scan.

Thus, in operation a user may view and select specific ultrasound images and files to be converted and exported from the ultrasound system 10 or 100 to the external media using, for example, the user scanner view control portion 304 and ultrasound image export process described herein. A user also may search/view the ultrasound images or files transferred or already stored on the medium/media (e.g., DVD) using the media view control portion 306. The scanner image control portion 308 allows a user to select and view general operating parameters, such as the source and destination for the export.

Figure 6:
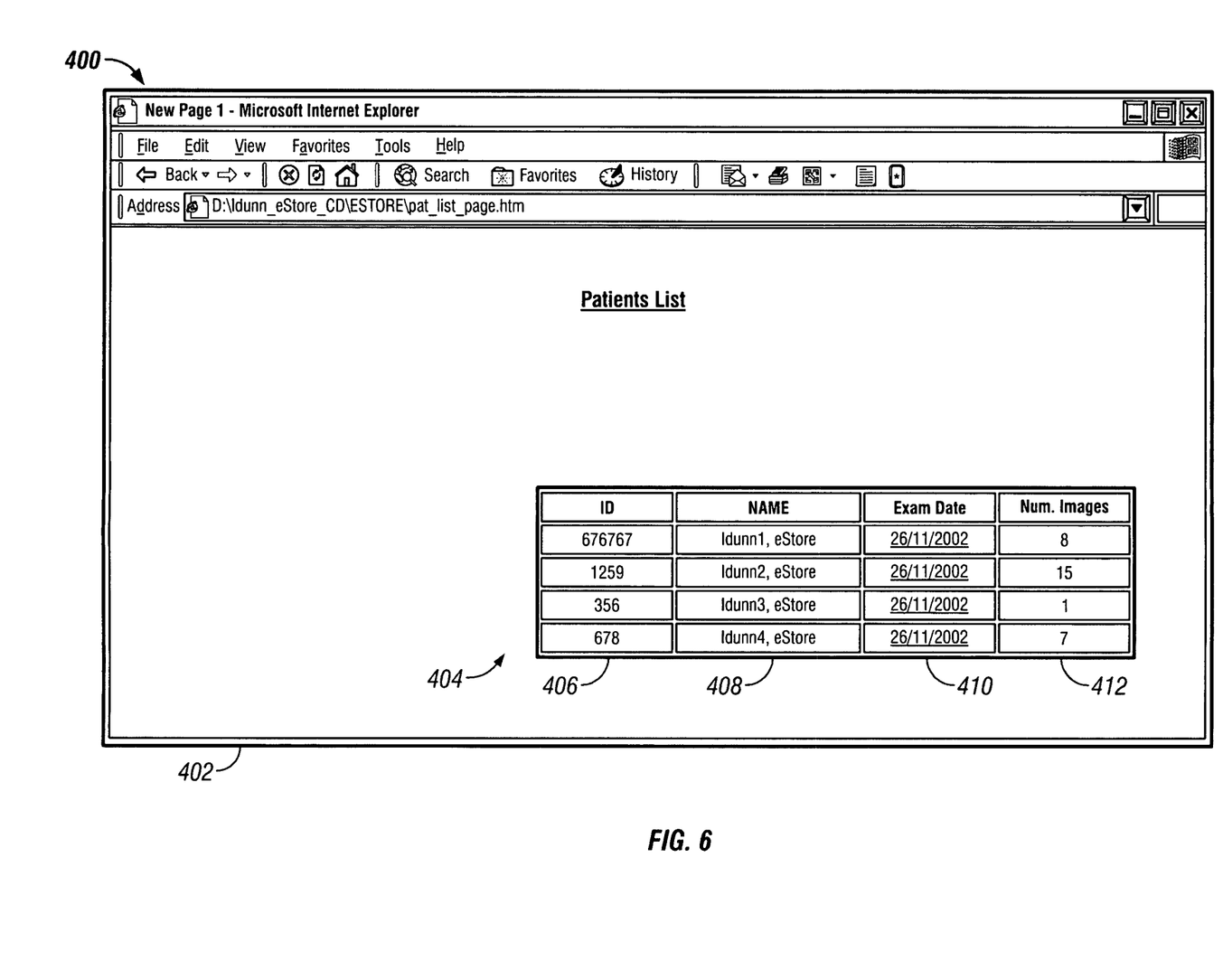
FIG. 6 is an exemplary embodiment of another user interface for access by a user device and displaying a selection screen.
Figure 7:
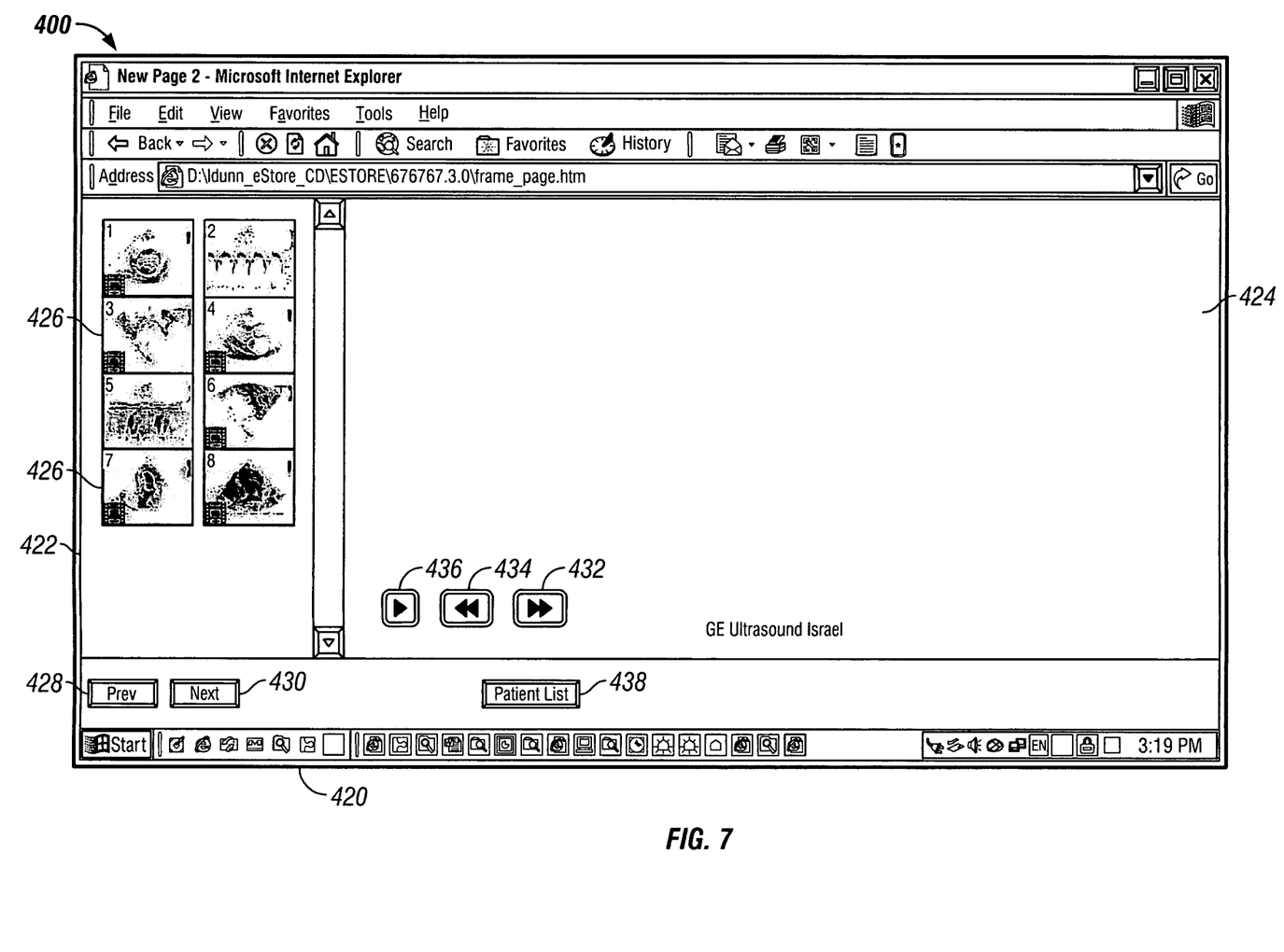
FIG. 7 is an exemplary embodiment of the user interface of FIG. 6 displaying a viewing screen.

After the ultrasound images or files are stored on the medium/media or on a remote device, which for example, may be later accessed to transfer the ultrasound images or files to the medium/media, a user interface 400 may be provided for viewing the ultrasound images with a user device (e.g., computer) as shown in FIGS. 6 and 7. The user interface 400 may be self executing, for example, when a CD ROM having the transferred ultrasound images or files is loaded in a CD ROM drive of a computer. Specifically, FIG. 6 is an exemplary embodiment of the user interface 400 displaying a selection screen/page 402 that may be displayed on a screen of a user device. The selection screen/page 402 allows a user to determine specific ultrasound data (e.g., ultrasound images) to be accessed and viewed. For example, a patients list 404 may include an ID column 406 having identification information for each image file (e.g., identification number for stored image(s) relating to a patient), a Name column 408 having a name (e.g., patient name) corresponding to each of the ID numbers, an Exam Date column 410 identifying the exam date corresponding to the image file and a Num. Images column 412 identifying the number of images associated with the image file. A user may select a particular image file, for example, by highlighting the image file of interest and selecting the file (e.g., using a pointer on the screen to select the date corresponding to the image file and selecting that date).

Once an image file is selected, in an exemplary embodiment, the user interface 400 displays a viewing screen/page 420 as shown in FIG. 7. The viewing screen/page 420 includes a preview portion 422 and viewing portion 424. The preview portion 422 allows a user to view, for example, thumbnail images 426, which may be selected for viewing (e.g., enlarged viewing) in the viewing portion 424. A user may also sequentially view the images using a Prev Image selection member 428 to view a previous image and Next Image selection member 430 to view the next image. It should be noted that a cine loop of images also may be viewed if available in the preview portion 422 and a user selects a play selection member 436 to view the cine loop. When viewing cine loops a forward arrow selection member 432 and a back arrow selection member 434 may be used by a user to fast-forward or reverse the cine loop, respectively. To return to the selection screen/page 402 a user selects a Back to Patient List selection member 438. Thus, the user interface 400 allows a user to easily view ultrasound images on devices (e.g., a laptop computer) external to the ultrasound systems 10 and 100.

It should be noted that data or information other than ultrasound images or files may be provided as part of the ultrasound data, which is also converted and exported. For example, calibration information may be stored in connection with each ultrasound image for use in performing diagnostic measurements. These diagnostic measurements may be performed, for example, by a doctor using the user interface 400 displayed on his or her laptop computer. For example, the size of a fetal head may be estimated using the calibration information. As another example, the calibration information may be used is assessing the blood velocities in a Doppler scan mode in a cardiac application.

Figure 8:
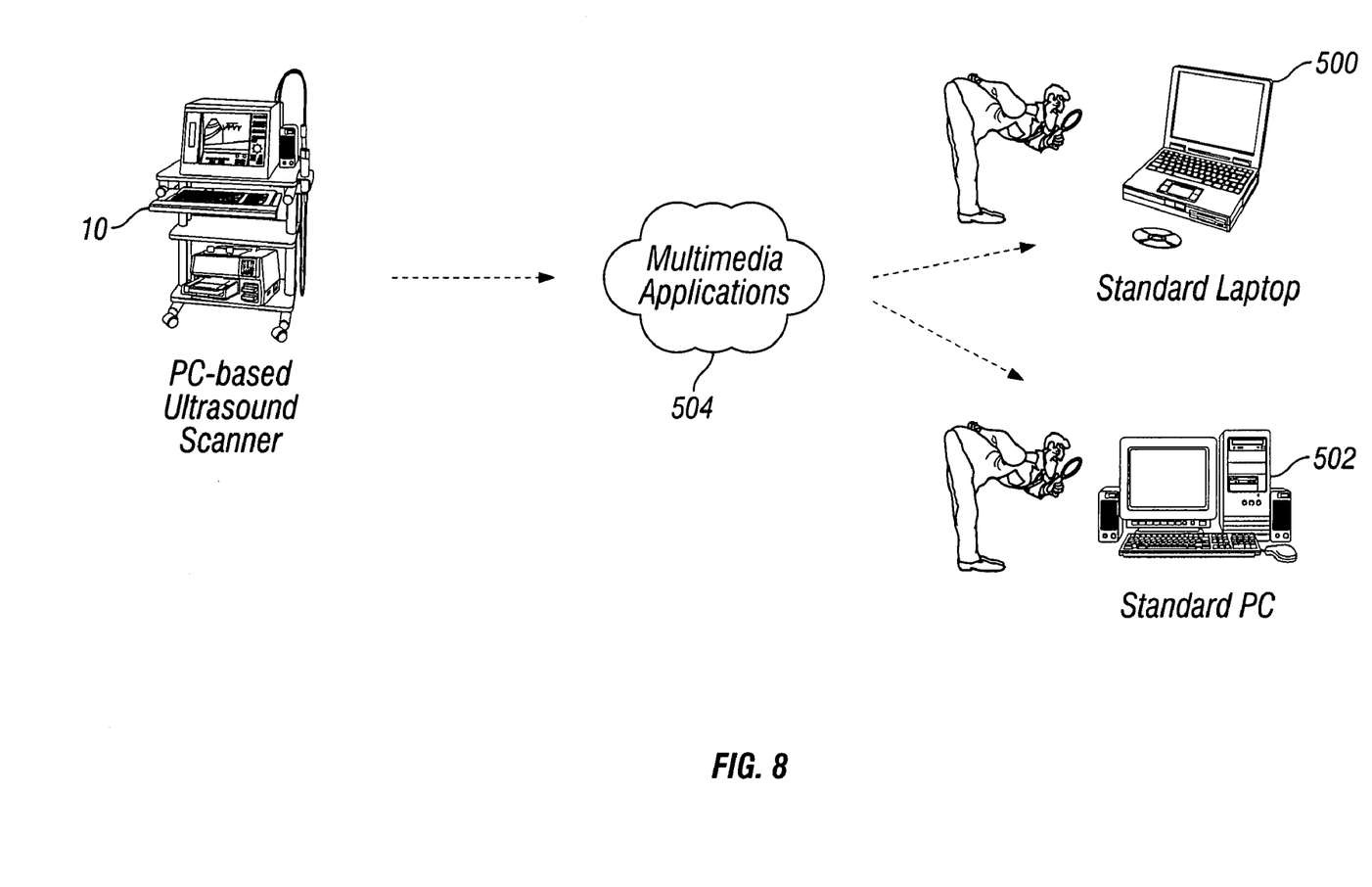
FIGS. 8 and 9 are block diagrams illustrating exemplary medium to which ultrasound data may be exported according to various embodiments of the present invention.
Figure 9:
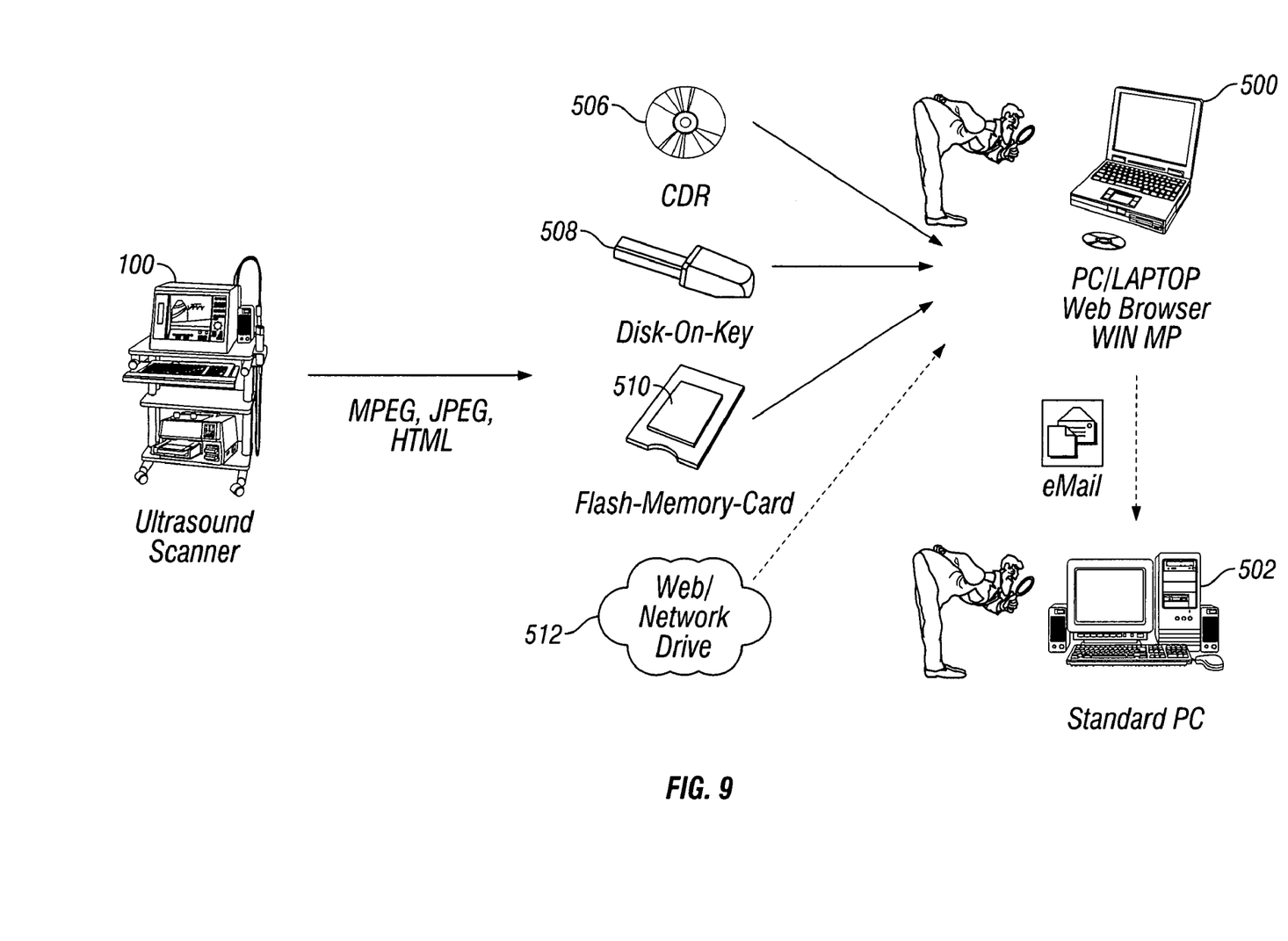

Thus, in operation, using the user interfaces 300 and 400 and the ultrasound image export process, ultrasound images or files may be converted and exported from an ultrasound system 10 or 100 and viewed by external user devices as shown in FIGS. 8 and 9. For example, as shown in FIG. 8 ultrasound images or files archived in the ultrasound system in a proprietary format or other specific format (e.g., DICOM format) are transferred using the ultrasound image export process to user devices, such as a networked laptop 500 or standard personal computer 502 (e.g., connected to the ultrasound system 10) via an application 504 having the user interface 300 for viewing, for example, ultrasound images with a user device having the user interface 400. It should be noted that the transfer of the images may be performed during or after the patient examination.

As another example, as shown in FIG. 9, the ultrasound images or files may be exported from an ultrasound system 100 and stored on media that is accessible using a user device, such as a laptop 500, and thereafter transferred (e.g., emailed) to a standard personal computer 502. In particular, and as described in detail herein, the ultrasound images or files are converted to a format (e.g., JPEG, MPEG, HTML, PDF, etc.) accessible by the user devices and stored on a medium/media readable by the user devices. These media may include, for example, a recordable CD ROM 506, an external storage device 508 (e.g., flash drive), a flash memory card 510, a network drive 512, an MOD (not shown) or a DVD (not shown). Thus, the ultrasound images or files are easily accessible and viewable on a plurality of user devices. It should be noted that the various embodiments of the present invention are not limited to exporting and storing ultrasound images or files in a particular format on a particular media for viewing on specific user devices as described herein. The various embodiments may be used to export and store ultrasound data (e.g., ultrasound images or files) in different formats on any suitable media for access and viewing using different user devices (e.g., Personal Digital Assistant (PDA), cellular telephone, etc.).

Figure 10:
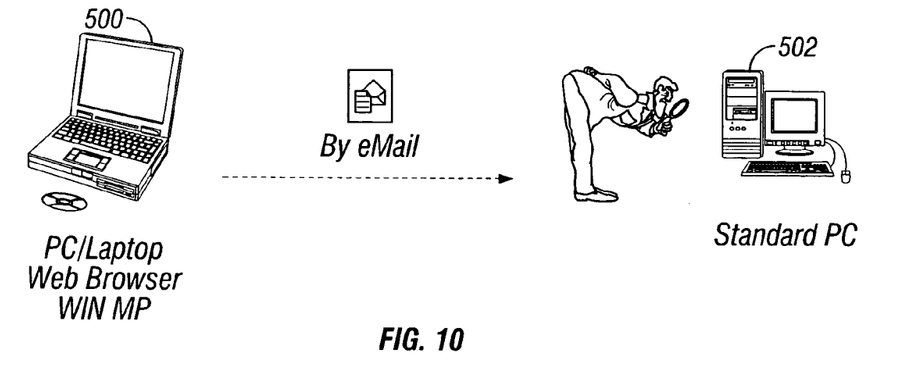
FIGS. 10 and 12 are block diagrams illustrating exemplary transferring processes for exported ultrasound data according to various embodiments of the present invention.
Figure 11:
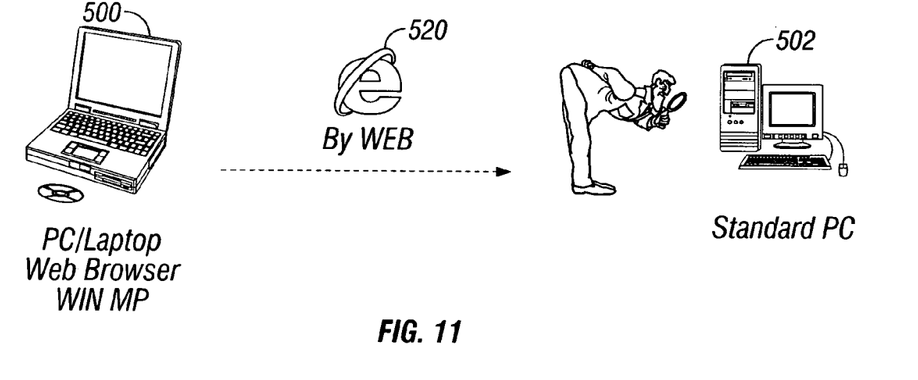

Thus, a user is not limited to accessing and viewing the ultrasound images or files on specific devices (e.g., ultrasound machines). For example, as shown in FIG. 10, ultrasound images or files stored on a CD ROM may be accessed using a laptop computer 500 and emailed to a standard personal computer 502 late at night from a doctor on duty at a hospital to a more experienced doctor at home. As another example, a patient may receive a CD ROM with ultrasound images of her baby, and may access the images using the laptop computer 500 and email them to friends and family for access using a standard personal computer 502. Alternatively, and as shown in FIG. 11, the ultrasound images or files may be uploaded from a laptop computer 500 and viewable via a user accessible website 520 using a standard personal computer 502.

Figure 12:
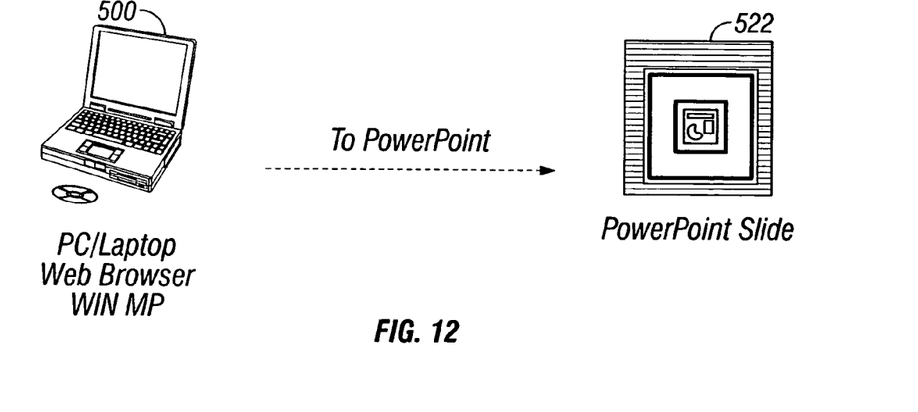

As another example, and as shown in Fig. 12, the ultrasound images or files may be viewed on a laptop computer 500 via a presentation application 522 having a slide show. A patient may then create a slide show of ultrasound images of her baby or a doctor may create a slide show for a presentation. It should be noted that a user is not limited to accessing and viewing the ultrasound images or files on specific devices via specific media as described in these examples, but the ultrasound images or files may be converted, exported and saved to any suitable medium/media for viewing with different user devices.

Thus, various exemplary embodiments provide for converting and exporting ultrasound data (e.g., ultrasound images or files) in different formats for easy viewing with different user devices that are not modality specific. The ultrasound data may be stored on different medium/media in different formats based upon the requirements of the specific user device.

While the invention has been described in terms of various specific embodiments, those skilled in the art will recognize that the invention can be practiced with modification within the spirit and scope of the claims.

What is claimed is:

1. A method for providing ultrasound data for access with a user device, comprising:
    accessing ultrasound data stored within an ultrasound system, the ultrasound data stored in an ultrasound system readable format;
    converting the ultrasound system readable format data to a user device readable format data for export from the ultrasound system and access via a user device; and
    storing the user device readable format data on a removable medium within the ultrasound system, the removable medium configured to be accessed by the user device and including an embedded viewer configured to allow viewing of the user device readable format data.

2. A method in accordance with claim 1, wherein the user device readable format comprises at least one of JPEG, MPEG, HTML and PDF format.

3. A method in accordance with claim 1, wherein the user device comprises a device remote from the ultrasound system.

4. A method in accordance with claim 1, further comprising configuring the user device readable format data for automatic viewing upon access by a user device.

5. A method in accordance with claim 1, further comprising providing a user interface in combination with the exported user device readable format data accessible by the user device for viewing the user device readable format data.

6. A method in accordance with claim 1, further comprising providing a user interface in combination with the ultrasound system for controlling the converting, and wherein the user interface is configured to allow for selection of a source and destination for the ultrasound data, and wherein the ultrasound system readable format data is converted to the user device readable format based upon the selected destination.

7. A method in accordance with claim 1, wherein the ultrasound data comprises at least one of ultrasound images and ultrasound image cine loops.

8. A method in accordance with claim 1, wherein the converting comprises converting the ultrasound data from a pixel format to at least one of a JPEG, MPEG, HTML and PDF format.

9. A method for exporting data from an ultrasound system for access with a user device, the method comprising:
    displaying ultrasound data representing ultrasound images stored within an ultrasound system;
    selecting at least one of the ultrasound images for exporting to an external medium;
    selecting a source and destination for the at least one ultrasound image, the destination defining the external medium;
    converting the at least one image to a non-DICOM format accessible by a user device;
    storing the non-DIMOM formatted image on a removable external medium using a recording device of the ultrasound system; and
    providing an embedded vieweron the removable external medium, the embedded viewer configured to allow viewing of the non-DIMOM formatted image.

10. A method in accordance with claim 9, wherein the converting comprises converting the at least one ultrasound image from an ultrasound system readable format to a user device readable format.

11. A method in accordance with claim 9, further comprising determining the ultrasound images to transfer based upon patient information.

12. A method in accordance with claim 9, further comprising searching the ultrasound data based upon a user defined search.

13. A method in accordance with claim 12, wherein a plurality of fields are provided for defining the search, the plurality of fields comprising at least one of identification information, name, birthdate, age and sex.

14. A method in accordance with claim 12, wherein a predetermined set of search criteria is provided to define the search.

15. A method in accordance with claim 9, further comprising displaying ultrasound data representing ultrasound images transferred to the external medium.

16. A method in accordance with claim 9, further comprising accessing the transferred ultrasound images using an interface provided in combination with the external medium.

17. A method in accordance with claim 9 further comprising using one of a CD writer and a DVD writer to store the formatted image on the removable external medium.

18. A user interface for an ultrasound system comprising:
    a scarmer view control portion for selecting ultrasound data for converting and transferring to an external medium;
    a media view control portion for viewing ultrasound data converted and transferred to the external medium; and a scanner image control portion for controlling the conversion and transfer of the ultrasound data to the external medium, the external medium including an embedded viewer configured to allow viewing of the ultrasound data.

19. A user interface in accordance with claim 18, wherein the scanner view control portion comprises a plurality of search fields for defining a search for ultrasound data.

20. A user interface in accordance with claim 18, wherein the scanner image control portion comprises a source field and a destination field to define the source of the ultrasound data and destination for the converted data.

21. A user interface in accordance with claim 18, wherein the ultrasound data is converted from an ultrasound system readable format data to a user device readable format data for export from the ultrasound system and access via a user device.

22. A user interface in accordance with claim 18, furthering comprising a selection interface in combination with the external medium to select transferred ultrasound data to access with a user device.

23. A computer readable medium having resident thereon a set of computer readable instructions conflaured to instruct a processor in an ultrasound system to:

store on a removable external medium at least one ultrasound image formatted for access by a user device, the at least one ultrasound image stored using a recording device of the ultrasound system and removable therefrom; and automatically display on the user device using an interface provided as part of an embedded viewer the at least one ultrasound image when accessed by a reading device of the user device having the medium therein.

24. A medium in accordance with claim 23, wherein the interface comprises a preview portion and viewing portion, the preview portion allowing a user to select ultrasound images stored on the medium and for viewing in the viewing portion.

* * * * *